United States Patent
Ikhlef

(10) Patent No.: US 10,492,746 B2
(45) Date of Patent: Dec. 3, 2019

(54) SPHERICAL DETECTOR FOR CT SYSTEM

(71) Applicant: FMI Medical Systems Co., Ltd., Zhejiang (CN)

(72) Inventor: Abdelaziz Ikhlef, Hudson, OH (US)

(73) Assignee: FMI Medical Systems Co., Ltd., Zhejiang (CN)

( * ) Notice: Subject to any disclaimer, the term of this patent is extended or adjusted under 35 U.S.C. 154(b) by 172 days.

(21) Appl. No.: 15/889,690

(22) Filed: Feb. 6, 2018

(65) Prior Publication Data
US 2019/0239833 A1    Aug. 8, 2019

(51) Int. Cl.
*A61B 6/03*    (2006.01)
*A61B 6/00*    (2006.01)

(52) U.S. Cl.
CPC .......... *A61B 6/4266* (2013.01); *A61B 6/4233* (2013.01); *A61B 6/4435* (2013.01); *A61B 6/4291* (2013.01)

(58) Field of Classification Search
CPC ... A61B 6/4233; A61B 6/4266; A61B 6/4291; A61B 6/4435
See application file for complete search history.

(56) References Cited

U.S. PATENT DOCUMENTS

| | | | |
|---|---|---|---|
| 5,912,938 A * | 6/1999 | Dobbs | G01N 23/046 378/19 |
| 7,149,284 B2 | 12/2006 | Ikhlef | |
| 2003/0016779 A1* | 1/2003 | Pohan | A61B 6/035 378/19 |
| 2008/0101542 A1 | 5/2008 | Ikhlef et al. | |
| 2012/0321041 A1 | 12/2012 | Ikhlef et al. | |
| 2012/0328076 A1 | 12/2012 | Ikhlef | |
| 2015/0071401 A1* | 3/2015 | Lacey | G01N 23/046 378/19 |

* cited by examiner

*Primary Examiner* — Mark R Gaworecki
(74) *Attorney, Agent, or Firm* — Fishman Stewart PLLC

(57) ABSTRACT

A CT system includes a rotatable gantry having, an x-ray tube having a focal spot, and a detector assembly positioned to receive the x-rays that pass through the object. The detector assembly includes an array of module support structures positioned along a channel direction, each module support structure having module support surfaces extending along the Z-axis, the array including a first module support structure and a second module support structure that are side-by-side, and a plurality of detector modules positioned on each module support structure and having collimating elements that are generally aligned toward the focal spot. Each of the first and second module support structures includes two steps symmetrically disposed along the Z-axis, such that a first gap between the detector modules of the first and second module support structures at a center of each is less than a second gap formed at each step.

20 Claims, 8 Drawing Sheets

SPHERICAL DETECTOR FOR CT SYSTEM

TECHNICAL FIELD

This disclosure relates generally to diagnostic imaging and, more particularly, to an apparatus and method of fabricating an arcuate detector for a CT system.

BACKGROUND

Typically, in CT imaging systems, a rotatable gantry includes an x-ray tube, a detector, a data acquisition system (DAS), and other components that rotate about a patient that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into photons within the scintillator, and then to electrical signals within the photodiode. The electrical signals are digitized and then received within the DAS, processed. The processed signals are transmitted via a slipring (from the rotational side to the stationary side) to a computer or data processor for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector.

Imaging data may be obtained using x-rays that are generated at a single polychromatic energy spectrum. However, some systems may obtain multi-energy images that provide additional information for generating images, using dual energy or fast KV switching.

Third generation multi-slices CT scanners are typically built with detectors made of scintillator/photodiodes arrays. The detectors are positioned along an arc where a focal spot is the center of the corresponding circle. The material used in these detectors generally use scintillation crystal/photodiode arrays, where the scintillation crystal absorbs X rays and converts the absorbed energy into visible light. A photodiode is used to convert the light to an electric current. The reading is proportional and linear to the total energy absorbed.

In recent years the development of volumetric or cone-beam CT technology has led to an increase in the number of slices used in CT detectors. The detector technology used in large coverage CT enables increased coverage in patient scanning, by increasing the area exposed. In CT detectors, the increase of the number of slices results in an increase in the width of the detector in Z-axis (e.g., along a length of the patient).

The x-ray detectors of current state of the art CT systems are generally composed of a two-dimensional (2D) array of scintillating pixels, coupled to a 2D array of Si photodiodes. A typical detector includes, as examples, an array of 16, 32 or 64. However, in recent years, the need for cardiac imaging has become of increasing interest, and to include imaging of the heart within one rotation. To image the heart in one rotation, the corresponding detector size needs is approximately 140 mm to 160 mm at iso-center to cover the full organ in one rotation (equivalent to a detector with 256 slices, in this example).

However, building such a detector as single mono-structure includes significant challenges. For a detector of 256 slices and perhaps an arc of 1000 channels, a total of 256,000 pixels results in the total detector. Such a massive mono-structure inevitably will include manufacturing flaws that need repair prior to shipping as new product, such as when bad pixels are detected, or when poor image quality is observed. In addition, the detector pixels include collimating elements that are directed toward the focal spot. However, collimation may need to account for the arc in not only the channel direction, but in the Z or slice direction, as well.

Some proposed designs include using mini-modules that may be fabricated, and placed on the arc both in the channel and Z or slice directions. However, placement of mini-modules on such arcs can result in geometric challenges that can result in gaps that occur between modules.

Thus, there is a need to improve CT detectors for large Z-coverage systems.

BRIEF DESCRIPTION

The disclosure is directed toward an apparatus and method of fabricating a spherical CT detector.

A CT system includes a gantry having an opening for receiving an object to be scanned along a Z-axis of the gantry, the gantry rotatable about a channel direction of the gantry, an x-ray tube having a focal spot from which x-rays emit, and a detector assembly positioned to receive the x-rays that pass through the object. The detector assembly includes an array of module support structures positioned along the channel direction, each module support structure having module support surfaces extending along the Z-axis, the array including a first module support structure and a second module support structure that are side-by-side, and a plurality of detector modules positioned on each module support structure and having collimating elements that are generally aligned toward the focal spot when positioned on a respective module support surface. Each of the first and second module support structures includes two steps symmetrically disposed along the Z-axis, such that a first gap between the detector modules of the first and second module support structures at a center of each is less than a second gap formed at each step.

A detector assembly for a CT system includes an array of module support structures positioned along a channel direction of the CT system, each module support structure having module support surfaces extending along a Z-axis of the CT system, the array including a first module support structure and a second module support structure that are side-by-side, and a plurality of detector modules positioned on each module support structure and having collimating elements that are generally aligned toward a focal spot of the CT system when positioned on a respective module support surface. Each of the first and second module support structures includes two steps symmetrically disposed along the Z-axis, such that a first gap between the detector modules of the first and second module support structures at a center of each is less than a second gap formed at each step.

A method of manufacturing a CT detector includes positioning an array of module support structures along a channel direction of a CT system, each module support structure having module support surfaces extending along a Z-axis of the CT system, the array including a first module support structure and a second module support structure that are side-by-side, and positioning a plurality of detector modules on each module support structure and having collimating elements that are generally aligned toward a focal spot of the CT system when positioned on a respective module support surface. Each of the first and second module support structures includes two steps symmetrically disposed along the Z-axis, such that a first gap between the detector modules of the first and second module support structures at a center of each is less than a second gap formed at each step.

Various other features and advantages will be made apparent from the following detailed description and the drawings.

DETAILED DESCRIPTION

The operating environment of disclosed embodiments is described with respect to a sixteen-slice computed tomography (CT) system. Embodiments are described with respect to a "third generation" CT scanner, however it is contemplated that the disclosed embodiments are applicable to other imaging systems as well, and for CT systems having more or less than the illustrated sixteen-slice system.

Figure 1:
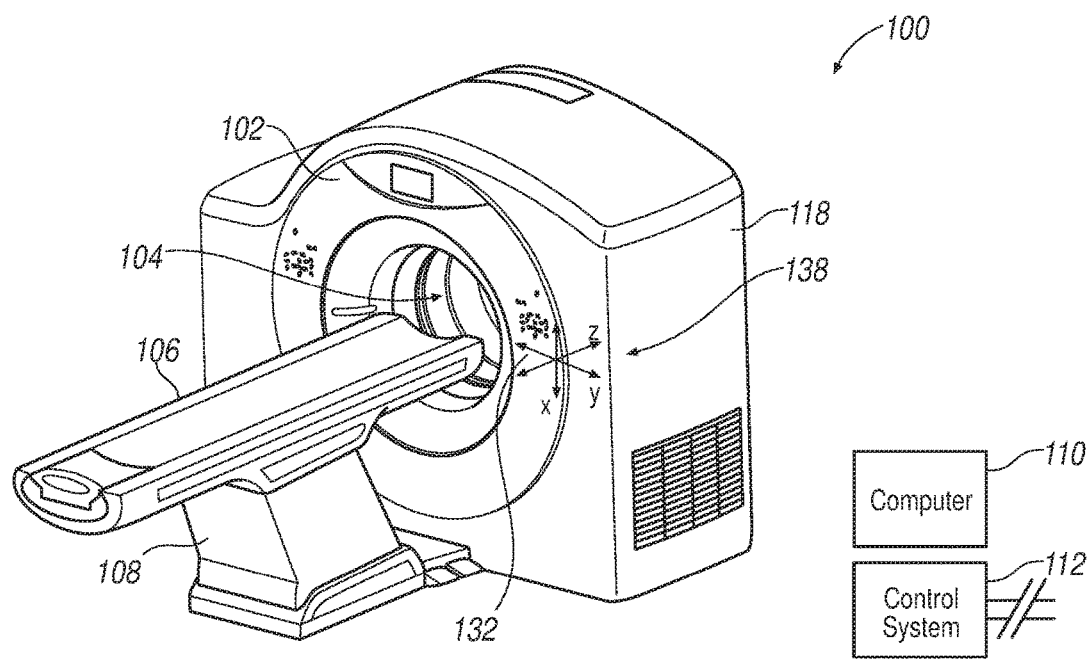
FIG. 1 is a perspective view of a CT imaging system.
Figure 2:
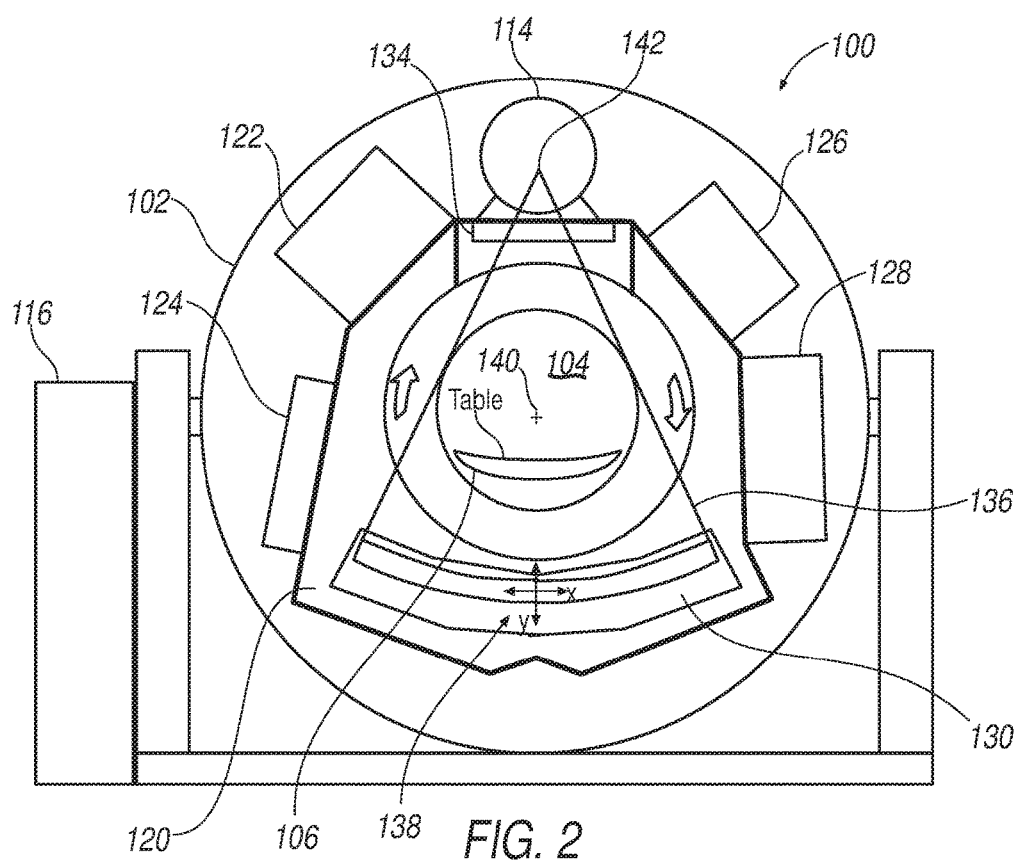
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction algorithms, or an image reconstructor may be provided as a separate processing unit. Control system 112 provides control commands for operating gantry 102, an x-ray tube 114, a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a generator 128, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is caused to rotate about the patient up to typically a few Hz in rotational speed, and table 106 is caused to move the patient axially within opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals are digitized and passed to DAS 124, and then to computer 110 where the data is further processed to generate an image. The imaging data may be stored on computer system 100 and images may be viewed. An X-Y-Z triad 138, corresponding to a local reference frame for components that rotate on rotatable base 120, defines a local directional coordinate systems in a gantry circumferential direction X, a gantry radial direction Y, and gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
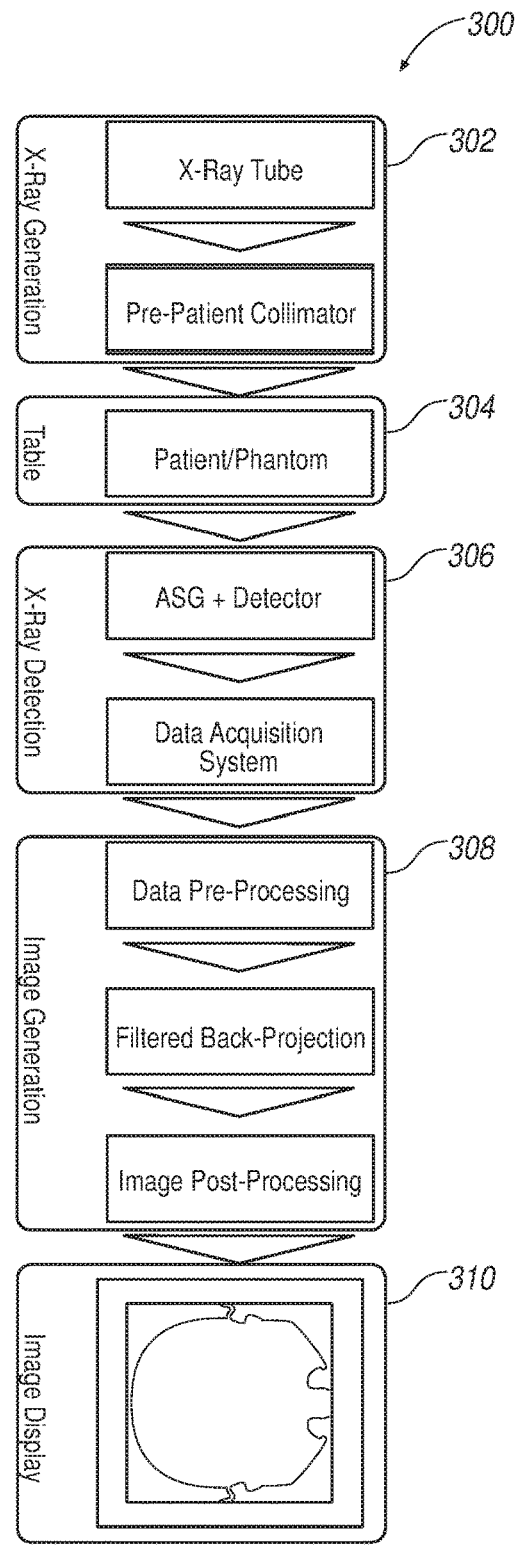
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which time table 106 passes 304 through opening 104 of gantry 102. In one example table 106 may have a patient thereon, and in another example a phantom may be used for calibration purposes.

X-ray detection 306 occurs when x-rays having emitted from x-ray tube 114 pass to detector assembly 130. An anti-scatter grid (ASG) prevents x-ray scatter (emitting for example from the patient as secondary x-rays and in a direction that is oblique to x-ray beam 136), by generally passing x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slipring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
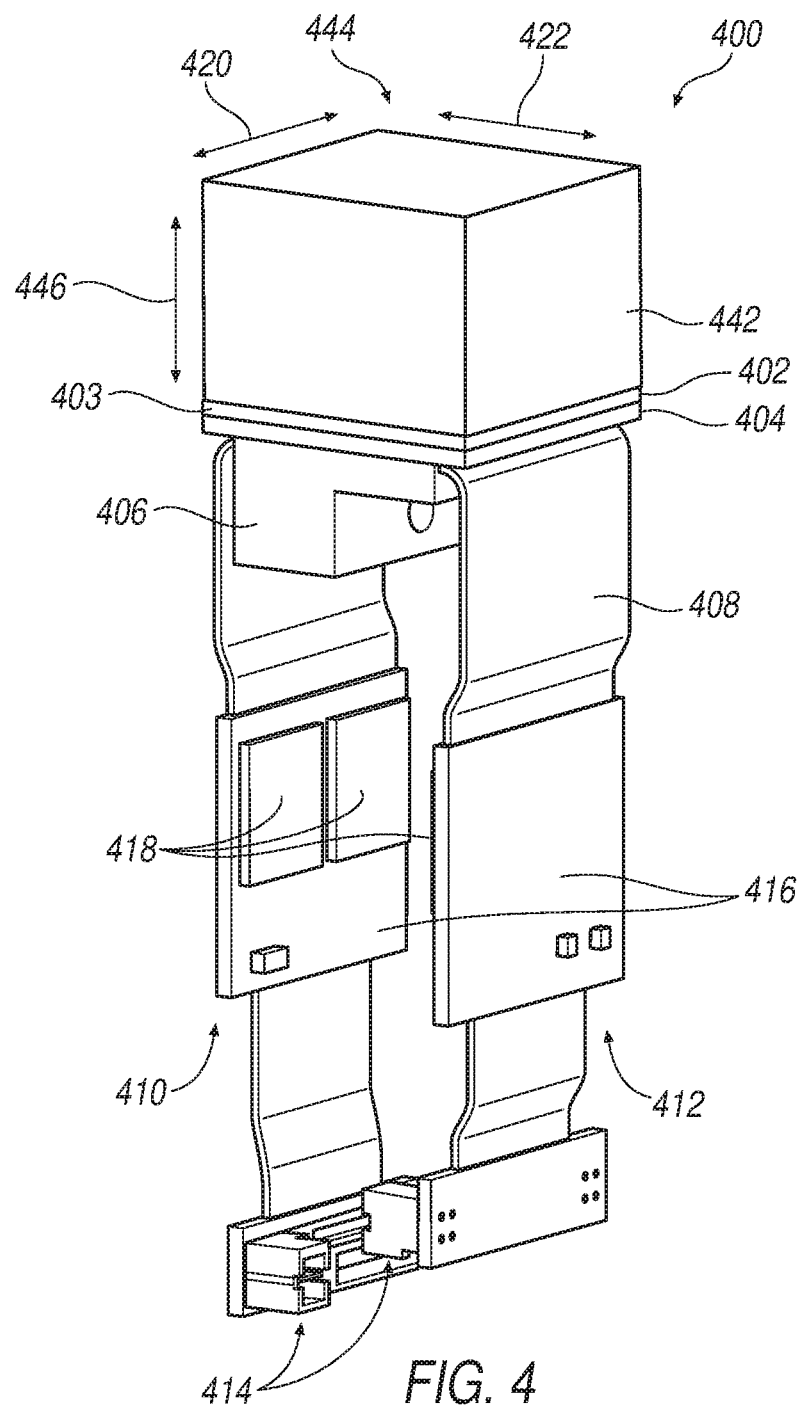
FIG. 4 illustrates a module or mini-module having been assembled according to the disclosure.

FIG. 4 illustrates a module or mini-module 400 having been assembled according to the disclosure. Module 400 includes a grid of pixelated scintillators or scintillating array 402 positioned on a substrate 404, having a photodiode 403 therebetween, the photodiode having an array of surfaces that correspond with the grid of pixelated scintillators. A module support structure or alignment block 406 mechanically supports module 400, as will be further described (and only a portion of which is visible in FIG. 4). Positioned between alignment block 406 and substrate 404 is a flex circuit 408, which wraps within module 400 and includes a first end 410 and a second end 412. Each end 410, 412 includes electrical connectors 414, a circuit board or electronics package 416, ASIC or processors 418, and other associated electronic components (not shown). Module 400, when placed on a gantry of a CT system, such as system 100 above, has an orientation of a Z or slice direction 420 and an X or channel direction 422.

FIG. 4 illustrates a basic unit of the detector called, in one example, a mini-module. In this example, the mini-module includes a 32×32 pixel crystal array on photodiode, and the equipment used to digitize the signal and as described above. To complete the mini-module, an anti-scatter grid (ASG) 442 is glued or otherwise attached to a surface of the array and an alignment and mounting block to the back of the photodiode substrate. However, in one example, to attach the 2D ASG, protrusions or notches are added on the top reflector, forming grooves (not shown) which will receive the ends of the 2D anti-scatter grid, allowing them to be aligned during the attachment and curing process.

An anti-scatter grid 442 having a plurality of plates 444 is positioned on upper surface 424 of scintillating array 402. Plates 444 are positioned proximate one another along a direction 446, but plates are not individually illustrated for visual purposes. In the example shown, anti-scatter grid 442 is a monolithic device having plates that extend in X or channel direction 422. Anti-scatter grid 442 in the illustrated example may be fabricated using a plurality of tungsten plates, or as another example may be fabricated using 3D printing technology and having high density materials such as tungsten or other x-ray absorbing materials therein. Accordingly, in one example, anti-scatter grid 442 is a two-dimensional (2D) collimator with plates 444 spaced from one another having a spacing that corresponds with a spacing of each of pixels 430. Such spacing may correspond with X or channel direction 422.

Plates 444 may thereby be fabricated in anti-scatter grid 442 to be slightly non-parallel to one another so that each may be directed and approximately aimed toward a focal spot of a CT system. For instance, referring back to FIG. 2, modules 400 may be positioned accordingly within CT detector assembly 130 and on gantry 102, having each plate 444 extending along a length and in direction 446 such that, when CT detector 130 is positioned in CT system 100, the length of plates 444 extend 446 approximately toward focal spot 142 of CT system 100.

Being a monolithic piece, anti-scatter grid 442 may be mechanically and precisely located having one of plates 444 on scintillating array 402. As such, anti-scatter grid 442 may be placed extremely accurately, within typically a few μm of desired location, by having both anti-scatter grid 442 and location notches on scintillating array 402 being fabricated with high tolerance control. That is, because each anti-scatter grid 442 is fabricated having a high and tight tolerance, and likewise notches may be fabricated having high and tight tolerances, then the placement of anti-scatter grid 442 with respect to pixels 430 may likewise be tightly controlled. Further, tolerances are controlled at a local level and global tolerances may not build up in the construction of a large monostructure such as CT detector 130.

In the above example, anti-scatter grid 442 is a 2D grid of plates 444. Thus, it may not be necessary to place plates 444 along Z or slice direction 420 to such as degree of high tolerance, given that the exemplary 2D collimator does not collimate, in this example, in the Z or slice direction 420. However, in one example anti-scatter grid 442 may be a three-dimensional (3D) grid, having plates extending in both channel and slice directions 422, 420. As such, placement in both directions 420, 422 may be controlled by including appropriate dimensional placement and sizing of notches in both X or channel direction 422, and Z or slice direction 420. That is, dimensional tolerances for both placement and size of notches may be appropriately controlled so that placement of anti-scatter grid 442 as a 3D grid may be controlled equally well in both directions.

According to the disclosure, mini-module 400 may be employed within detector assembly 130. That is, a plurality of mini-modules 400 may be used to form detector modules that extend along the Z-axis of the detector. Detector modules may then be placed side-by-side to form an arc along the X-axis of the detector assembly. As such, detector modules may be formed with a plurality of mini-modules 400, in order to simplify overall construction of the detector assembly. However, before illustrating the details as such, following is a visual illustration that will be subsequently referenced in order to understand some of the salient features of the disclosure, and the use of mini-module 400 as disclosed herein.

Figure 5A:
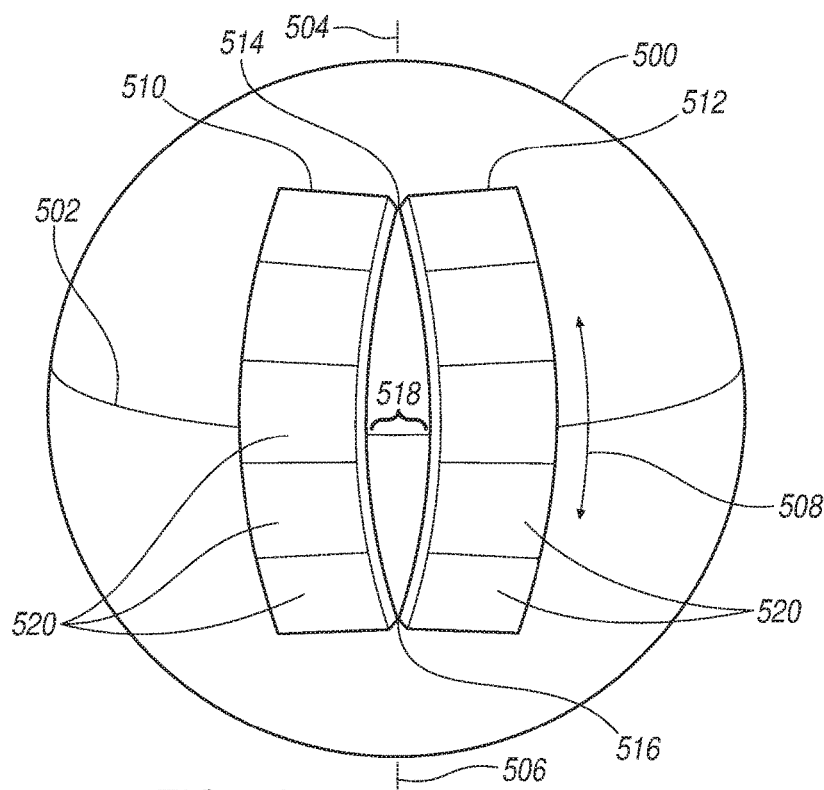
FIG. 5A illustrates a first exemplary set of rectangles on a spherical surface showing a first gap therebetween.
Figure 5B:
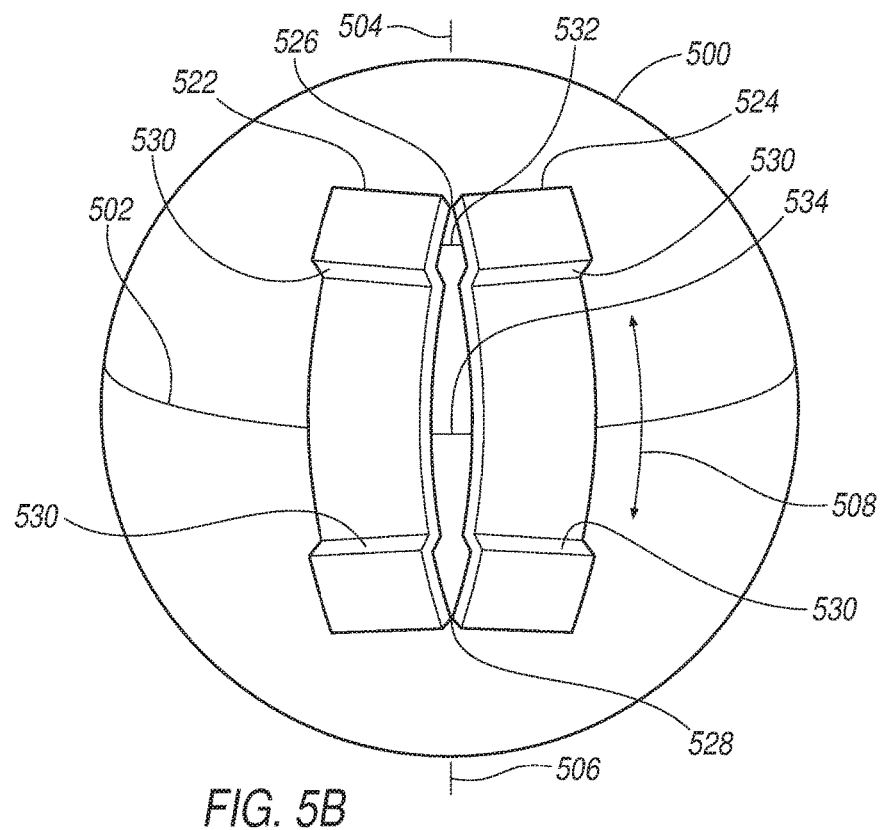
FIG. 5B illustrates a second exemplary set of rectangles in a spherical shape, but having a symmetric step therein, illustrating a reduced gap therebetween.

Referring to FIGS. 5A and 5B, a generally spherical structure 500 is shown, for illustration purposes only. Spherical structure 500 compares, generally, to system 100 as illustrated in FIGS. 1 and 2. Analogously, and for the purposes of illustration, an equator 502 is shown that correlates generally with the X-direction of system 100 and gantry 102. A "north" pole 504 and a "south" pole 506 form a rotational axis about which spherical structure 500 may be considered to rotate. An imaginary line between pole 504 and 506, about which spherical structure 500 rotates, corresponds with isocenter 140 of FIG. 2.

In general, and often within the art, system 100 of FIG. 2 represents generally a two-dimensional representation of the components, to include detector assembly 130. That is, commonly within the art detector assembly 130 extends "into" and/or "out of" the view seen in FIG. 2, and detector assembly 130 forms an arc extending in the x-direction such that detector surfaces (and corresponding collimator elements) are directed approximately toward focal spot 142. Typically, the detectors are not placed upon an arc extending in the "Z" or slice direction.

However, according to the disclosure, as detector length in "Z" (or in the slice direction) increases, there is an increased need to account for the corresponding arc that naturally forms about the detector for large Z coverage. That is, if the detector elements are not caused to face approximately orthogonal to focal spot 142, then image quality problems may arise particularly for detector elements positioned toward the extreme dimensions in Z.

Accordingly, and according to the disclosure, it is desirable to place a plurality of detector modules, such as using mini-module 400, to face approximately orthogonal to focal spot 142. However, doing so along the resulting arc (in the Z-direction) may result in a gap between detectors that are also placed side by side, as illustrated herein.

The effect is illustrated, referring again to FIGS. 5A and 5B. Equator 502 corresponds generally with X-direction of system 100 and gantry 102. A pole-pole coordinate 508 extends between pole 504 and pole 506, corresponding generally with a line of longitude on a globe, and corresponding approximately with the Z-direction within system 100.

Referring specifically to FIG. 5A, a first rectangle 510 and a second rectangle 512 are positioned on a surface of spherical structure 500. For illustration purposes, first and second rectangles 510, 512 are positioned such that their corners meet at a first location 514 and at a second location 516, and such that rectangles 510, 512 are equidistant from poles 504, 506. The illustrated example of FIG. 5A is analogous to two rectangular pieces of paper being adhered to a spherical surface, such as a globe. As can be seen in the illustration, although the first and second rectangles 510, 512 touch at respective locations 514, 516, due to curvature of the spherical surface a gap between the rectangles 510, 512 begins at each location 514, 516 and grows until a maximum gap 518 occurs at the equator 502. Each rectangle 510, 512 may thereby be considered a detector module to include a plurality of mini-modules 400. However, as can be seen in FIG. 5A, if mini-modules 400 are positioned side by side at locations 520 along pole-pole coordinate 508 and on a rectangular but curved surface, a substantial gap 518 would occur. One skilled in the art will recognize that, although the effect is exaggerated in FIG. 5A, it is nevertheless present, and its effect is enhanced for detector modules that extend yet further in Z, such as for 64 slice, 256 slice, and beyond.

In contrast, according to the disclosure, mini-modules 400 are positioned on a stepped structure, wherein the centermost mini-modules 400 are positioned closer to focal spot 142 than those along the edges. The effect is illustrated in FIG. 5B. As with FIG. 5A, a first rectangle 522 and a second rectangle 524 are positioned side-by-side such that their corners meet at a first location 526 and a second location 528. However, rather than each rectangle 522, 524 conforming to the spherical surface (as in FIG. 5A for rectangles 510, 512), instead each rectangle 522, 524 includes steps 530 that extend inward and toward a center of sphere 500. In such fashion and in a three-dimensional sense, steps 530 cause a step-function shift in the gap between detector modules. That is, starting from each location 526, 528, a gap 532 begins and grows in dimension until each step 530 is reached, at which point the gap decreases substantially, but then grows again until a local maximum 534 is reached at equator 502.

Figure 6:
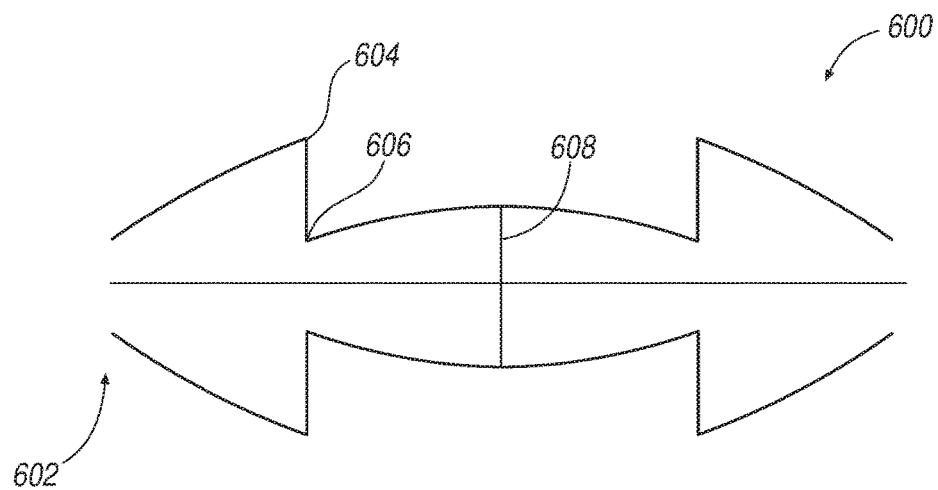
FIG. 6 illustrates a gap that occurs between the elements illustrated in FIGS. 5A and 5B, also representing an exemplary gap between detectors placed on an arc, that results according to the disclosure.

The effect is qualitatively illustrated in FIG. 6 as a hypothetical gap 600. Hypothetical gap 600 begins at a minimum 602 (and may be zero if corners actually touch, as in the example of FIG. 5B wherein corners 526 and 528 meet), and grows to a maximum 604, corresponding to step 530 of FIG. 5B. Hypothetical gap 600 decreases substantially due to steps 530 to reach a local minimum, at which point hypothetical gap 600 grows again, due to the curvature of spherical structure 500, reaching a local maximum 608 at the center, corresponding with equator 502 and gap 534 of FIG. 5B.

As such, disclosed is a detector module structure that corresponds with, and is analogous to, the discussion related to FIG. 5. Further, as illustrated in FIG. 5B and as discussed above, FIGS. 5A and 5B are meant for illustration purposes only and are not dimensionally relevant when considered on the scale of a system, such as CT system 100. Thus, FIG. 6 illustrates, according to the disclosure, that for modules support structures positioned side by side and including two steps symmetrically disposed along the Z-axis, a first gap between the detector modules of the support structure include a gap at a center of each that is less than a second gap formed at each step.

Figure 7:
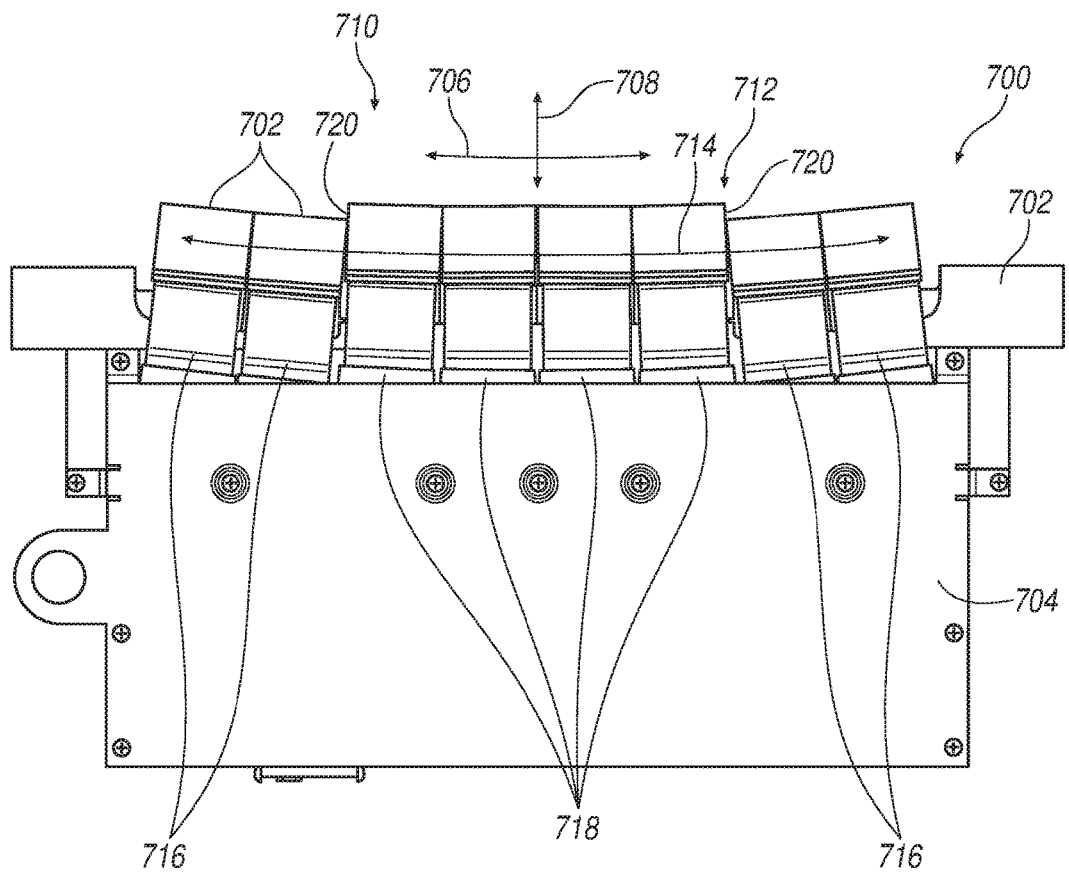
FIG. 7 illustrates a detector module having a plurality of mini-modules.

Referring to FIG. 7, a detector module 700 is disclosed having a plurality of mini-modules 400. Detector module 700 includes a support structure 702, on which mini-modules 400 are positioned, which corresponds with module support structure or alignment block 406 described above. Detector module 700 includes connection locations (not shown) to receive connectors 414, as well as an outer support structure 704, as well as other features for mounting and cooling each of mini-modules 400. Detector module 700 extends along a Z-axis 706, which corresponds with the Z-axis shown for system 100 of FIG. 1. Mini-modules 400 are positioned on a stepped surface, such that a step occurs in a Y-direction 708 at a first step location 710 and a second step location 712. As can be seen, support structure 702 extends along a general curvature 714, having the first two and the last two mini-modules 400 at approximately a first radial location 716, and the center four mini-modules 400 at approximately a second radial location 718, resulting in a step or height change 720.

Figure 8:
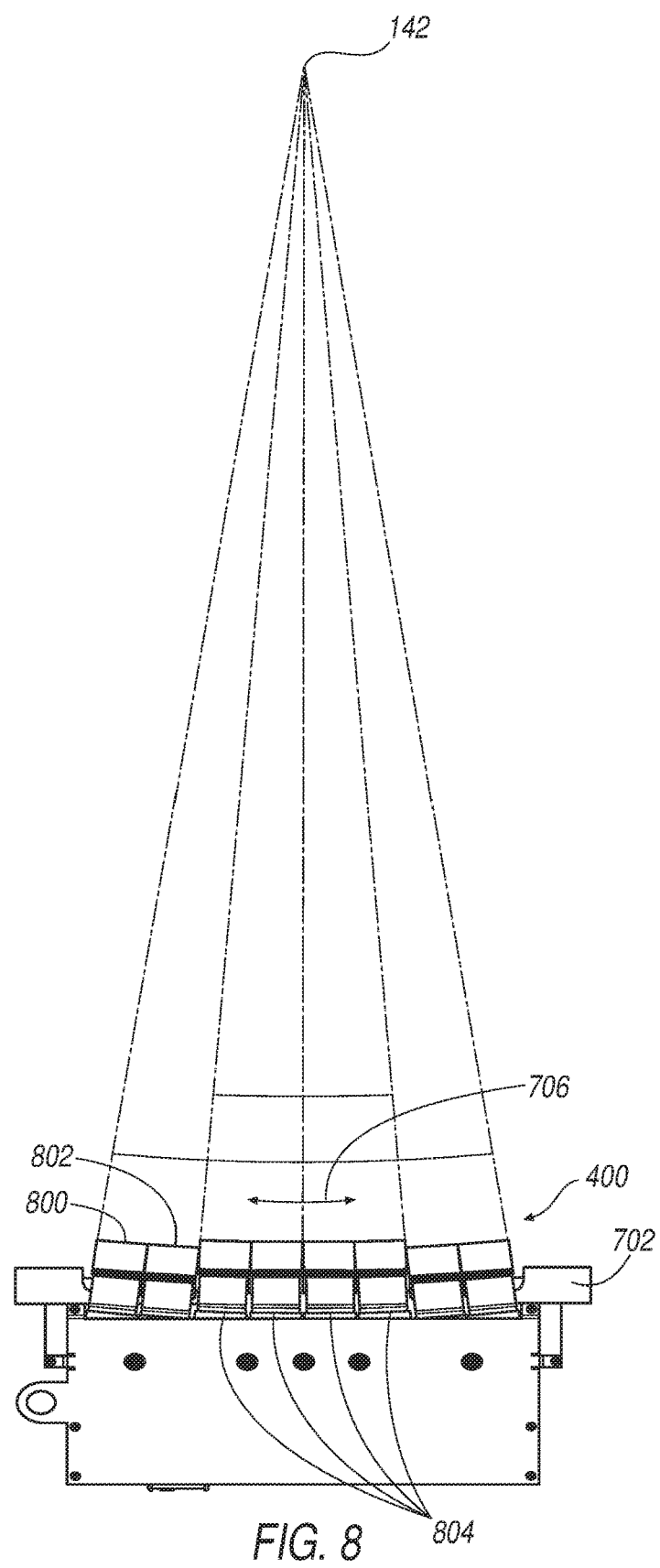
FIG. 8 illustrates a detector module shown in its position, within the system of FIG. 1, and with respect to the focal spot therein.

Referring to FIG. 8, detector module 700 is shown in its position, within system 100, and with respect to focal spot 142. Support structure 702 provides structural reference locations for each of mini-modules 400, thus it is contemplated that support structure 702 includes not only a step in height as described, but may also include individually machines flat surfaces that thereby direct each mini-module 400 toward focal spot 142. For instance, a first mini-module 800 and a second mini-module 802 may be positioned side-by-side along Z-axis 706 and at a first radial height with respect to center mini-modules 804. However, surfaces on which first and second mini-modules 800, 802 may be placed on surfaces that may not be necessarily coplanar or collinear with one another. Similarly, each of mini-modules 804, although placed approximately at the same distance from focal spot 142, may themselves be positioned on surfaces that are themselves each individually orthogonal to focal spot 142.

Figure 9:
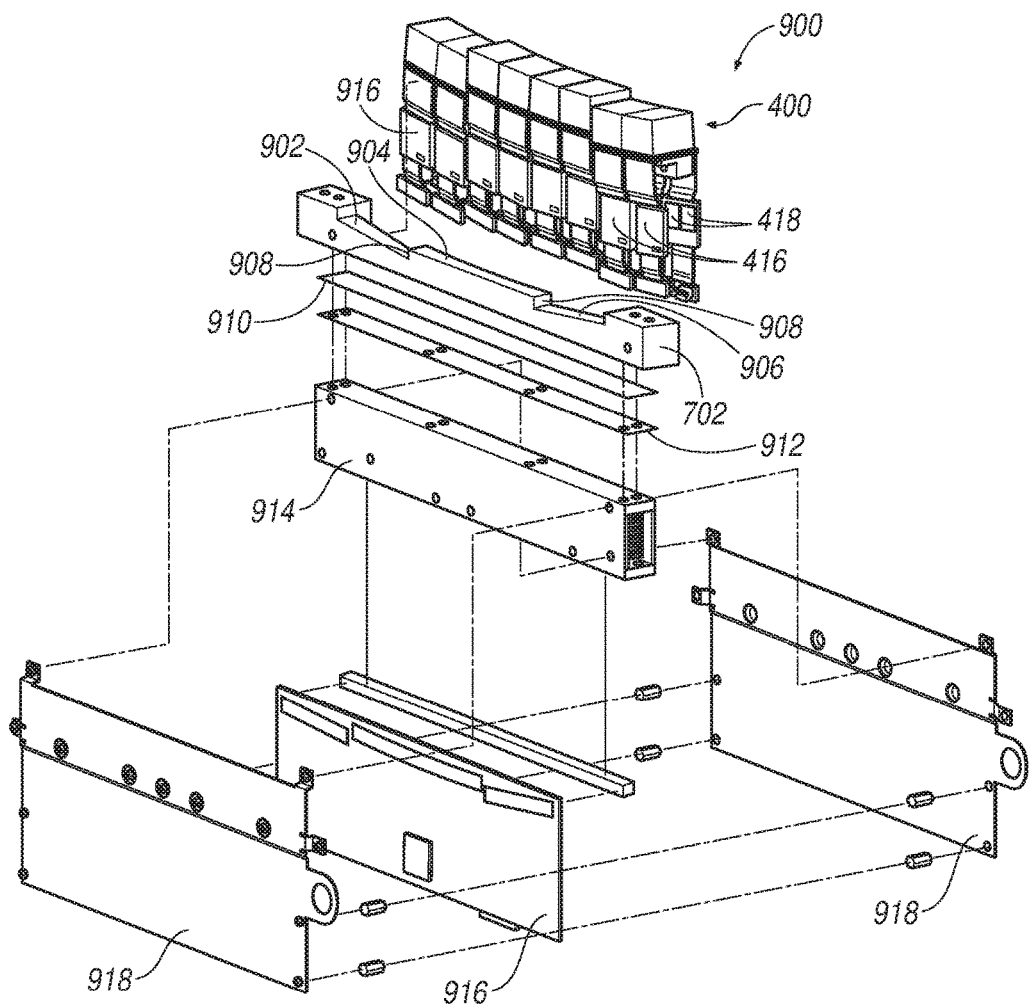
FIG. 9 illustrates an exploded and perspective view of the detector module of FIG. 7.

Referring to FIG. 9, and exploded and perspective view 900 of detector module 700 is shown. Mini-modules are shown proximate one another, and proximate support structure 702. Support structure 702 includes surfaces 902, 904, 906 which, as described above, include steps 908. And, as disclosed above, surfaces 902, 904, 906 may themselves include non-parallel surfaces such that each individual mini-module 400 may be directly aimed toward focal spot 142, regardless of which step it is positioned.

Also according to the disclosure, detector module 700 includes a heater 910 and a thermal barrier 912. Detector module 700 includes a heat sink 914, a FPGA printed circuit board 916, and support plates 918. As known in the art, thermal control is an important aspect of detector design, and thus heater 910 uniformly heats support structure 702, thereby maintaining each of mini-modules 400 at uniform temperature during calibration and use. Thermal barrier 912 reduces the propensity for heat to flow from ASIC or processors 418 on each of circuit board or electronics package 416. Heat sink 914 is thermally coupled to each circuit board or electronics package 416, preventing heat from flowing to support structure 702 to negatively affect thermal calibration or performance of the detectors.

Figure 10:
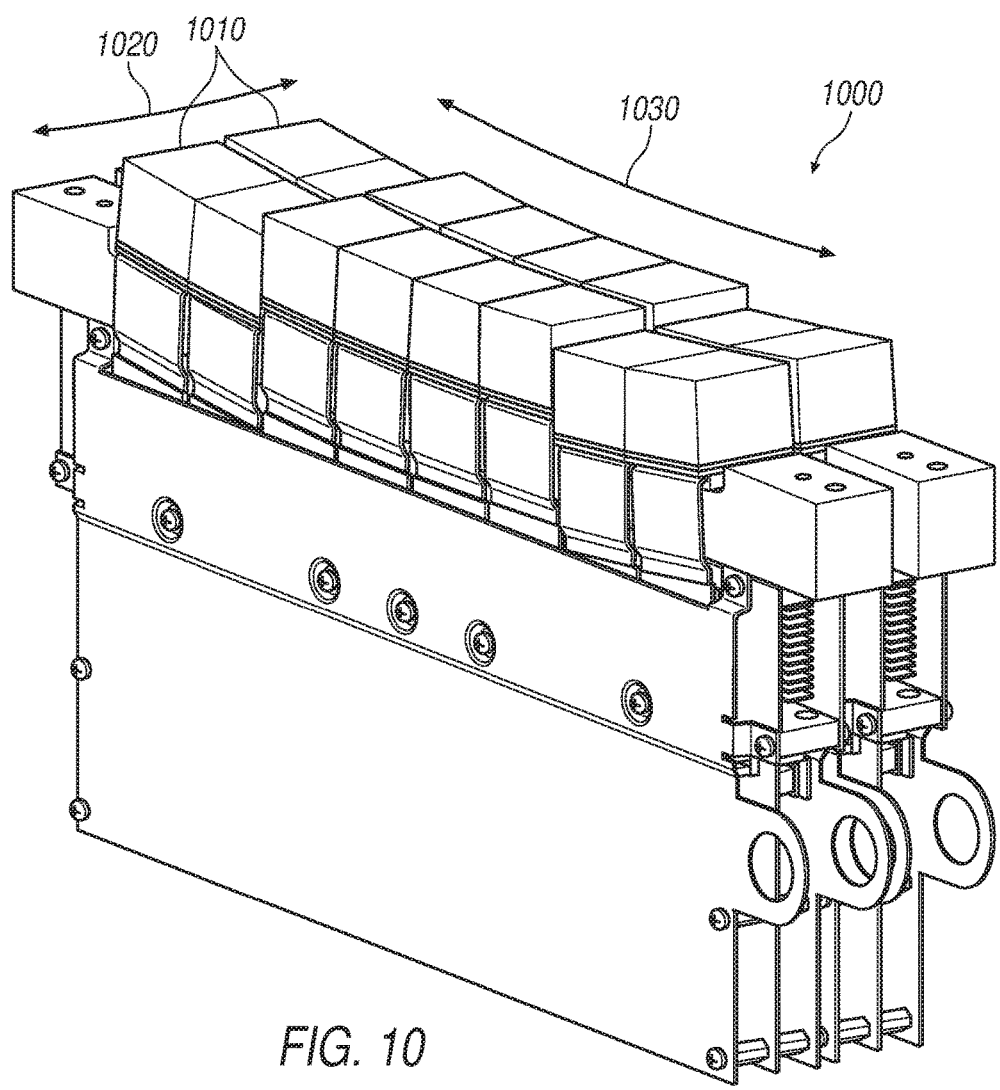
FIG. 10 illustrates detector modules positioned side by side, resulting in a reduced gap between modules at a center thereof, according to the disclosure.

Accordingly, referring to FIG. 10, two detector modules 1000 are illustrated, representing two 1010 of several detector modules that may be employed to form the disclosed spherical detector. As described, modules 1010 are positioned along an arc 1020 that corresponds with the x-direction shown in FIGS. 1 and 2. In addition, curvature along the Z-direction 1030 corresponds with the Z-direction of FIG. 1, as well.

As such, the disclosed detector module, having a step along Z-direction 1030, results in a reduced gap at the center (along Z-direction 1030), as would otherwise occur if no step were provided.

That is, disclosed is CT system 100 that includes gantry 102 having an opening 104 for receiving an object to be scanned along a Z-axis of gantry 102. Gantry 102 is rotatable about a channel direction of gantry 102. CT system 100 includes x-ray tube 114 having focal spot 142 from which x-rays emit. Detector assembly 130 is positioned to receive the x-rays that pass through the object. Detector assembly 130 includes an array 1000 of module support structures 406, 702 positioned along the channel direction, each module support structure 406, 702 having module support surfaces extending along the Z-axis, the array 1000 including a first module support structure 1010 and a second module support structure 1010 that are side-by-side. A plurality of detector modules 400 are positioned on each module support structure 406, 702 and having collimating elements that are generally aligned toward focal spot 142 when positioned on a respective module support surface. Each of the first and second module support structures 1000 includes two steps 710, 712 symmetrically disposed along the Z-axis, such that a first gap between the detector modules of the first and second module support structures 1000 at a center of each is less than a second gap formed at each step. The effect is illustrated as gaps 532 and 534, and occurs in modules 1010. Thus, according to the disclosure modules are placed side-by-side such that the steps cause a reduced gap at a center of the modules.

The first and second module support structures 1000 each include a first surface and a second surface at a first step height, as illustrated for instance in FIG. 7 on each end of the disclosed assembly 700, and the first and second module support structures 1000 each include a third surface at a second step height that is different from the first step height, the third step height occurring between the two ends of the disclosed assembly. As can be seen in, for instance, FIG. 7, the second height is closer to the focal spot than the first height. Also, the third surface passes through the center of each of the first and second module support structures, the first surface is at a first end of each of the first and second module support structures, and the second surface is at a second end, opposite the first end, of each of the first and second module support structures.

A first step of the two steps is between the third surface and the first surface, and a second step of the two steps is between the third surface and the second surface. The plurality of detector modules are positioned along an arc along the channel direction such that the plurality of detector modules are each equidistant to the focal spot.

Thus, since it is very difficult to build very large modules in a monolithic structure to cover 160 mm coverage or greater, to include manufacturing cost and reliability, smaller modules (mini-modules) are stacked along the z-axis, and thus achieve different coverage needs. The disclosed architecture achieves its goals of accurate and reliable construction by using an accurate process in stacking and classification of mini-modules, with a precise mechanical packaging which enable precise alignment, removability and reparability.

According to one example, the disclosed system includes mini-module elements that each include 32×32 arrays to achieve 256 slices by stacking them in a curved Z-axis. In the disclosed design both X-axis and Z-axis are curved to form a sphere where the focal spot is the center of the sphere. Using a sphere is motivated by the opportunity to use 2D anti scatter grid of a 32×32 array. Thus, if detectors were on a flat Z-axis plane, then it would be very difficult to build a 2D anti-scatter grid of, for instance, a 256×32 array. Thus, one concept behind this disclosure is to use mini-modules and stack them on a curved frame or structure along the Z-axis, to form a sphere. The disclosed modules include 32 slices and 32 channels, however it is contemplated that any array of slices and channels may be used. Further, although only two steps are disclosed along the Z-axis, forming two corresponding gaps along the Z-axis as shown in FIG. 6, it is contemplated that more than two steps may be used, resulting in still greater improvement and overall reduction in the collective gap between detector modules in a spherical arrangement.

Additional benefits that accrue, based on the disclosed detector, is a capability for modules to achieve up to 256 slices detectors, and beyond, to achieve different sizes of detector coverage without redesign of the mini-modules. The disclosed system includes optimized performance of the modules since the design facilitates early testing and classification. Every mini-module can be tested and classified and assigned a location in the detector based on its performance. The disclosed spherical detector structure enables one single 2D anti-scatter grid element—used in each mini-module. The disclosed design is compatible with thermal management based on conventional air convection. Other impacts of the disclosed subject matter on products such as a CT scanner are reparability of mini-module on site or in factories, testability of each mini-module before final installation into the overall structure, and improvement of image quality by enabling a 2D scatter rejection grid.

Disclosed is a CT system includes a gantry having an opening for receiving an object to be scanned along a Z-axis of the gantry, the gantry rotatable about a channel direction of the gantry, an x-ray tube having a focal spot from which x-rays emit, and a detector assembly positioned to receive the x-rays that pass through the object. The detector assembly includes an array of module support structures positioned along the channel direction, each module support structure having module support surfaces extending along the Z-axis, the array including a first module support structure and a second module support structure that are side-by-side, and a plurality of detector modules positioned on each module support structure and having collimating elements that are generally aligned toward the focal spot when positioned on a respective module support surface. Each of the first and second module support structures includes two steps symmetrically disposed along the Z-axis, such that a first gap between the detector modules of the first and second module support structures at a center of each is less than a second gap formed at each step.

Also disclosed is a detector assembly for a CT system includes an array of module support structures positioned along a channel direction of the CT system, each module support structure having module support surfaces extending along a Z-axis of the CT system, the array including a first module support structure and a second module support structure that are side-by-side, and a plurality of detector modules positioned on each module support structure and having collimating elements that are generally aligned toward a focal spot of the CT system when positioned on a respective module support surface. Each of the first and second module support structures includes two steps symmetrically disposed along the Z-axis, such that a first gap between the detector modules of the first and second module support structures at a center of each is less than a second gap formed at each step.

Further disclosed is a method of manufacturing a CT detector includes positioning an array of module support structures along a channel direction of a CT system, each module support structure having module support surfaces extending along a Z-axis of the CT system, the array including a first module support structure and a second module support structure that are side-by-side, and positioning a plurality of detector modules on each module support structure and having collimating elements that are generally aligned toward a focal spot of the CT system when positioned on a respective module support surface. Each of the first and second module support structures includes two steps symmetrically disposed along the Z-axis, such that a first gap between the detector modules of the first and second module support structures at a center of each is less than a second gap formed at each step.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A CT system comprising:
   a gantry having an opening for receiving an object to be scanned along a Z-axis of the gantry, the gantry rotatable about a channel direction of the gantry;
   an x-ray tube having a focal spot from which x-rays emit; and
   a detector assembly positioned to receive the x-rays that pass through the object, the detector assembly comprising:
      an array of module support structures positioned along the channel direction, each module support structure having module support surfaces extending along the Z-axis, the array including a first module support structure and a second module support structure that are side-by-side; and
      a plurality of detector modules positioned on each module support structure and having collimating elements that are generally aligned toward the focal spot when positioned on a respective module support surface;
   wherein each of the first and second module support structures includes two steps symmetrically disposed along the Z-axis, such that a first gap between the detector modules of the first and second module support structures at a center of each is less than a second gap formed at each step.

2. The CT system of claim 1, wherein the first and second module support structures each include a first surface and a second surface at a first step height, and the first and second module support structures each include a third surface at a second step height that is different from the first step height.

3. The CT system of claim 2, wherein the second height is closer to the focal spot than the first height.

4. The CT system of claim 2, wherein:
   the third surface passes through the center of each of the first and second module support structures;
   the first surface is at a first end of each of the first and second module support structures; and
   the second surface is at a second end, opposite the first end, of each of the first and second module support structures.

5. The CT system of claim 2, wherein a first step of the two steps is between the third surface and the first surface, and a second step of the two steps is between the third surface and the second surface.

6. The CT system of claim 1, each detector module further comprising:
   a substrate;
   a photodiode positioned on the substrate;
   a scintillating array positioned on the photodiode; and
   the collimating elements aligned with a grid of pixels within the scintillating array.

7. The CT system of claim 1, wherein the plurality of detector modules are positioned along an arc along the channel direction such that the plurality of detector modules are each equidistant to the focal spot.

8. A detector assembly for a CT system comprising:
   an array of module support structures positioned along a channel direction of the CT system, each module support structure having module support surfaces extending along a Z-axis of the CT system, the array including a first module support structure and a second module support structure that are side-by-side; and
   a plurality of detector modules positioned on each module support structure and having collimating elements that are generally aligned toward a focal spot of the CT system when positioned on a respective module support surface;
   wherein each of the first and second module support structures includes two steps symmetrically disposed along the Z-axis, such that a first gap between the detector modules of the first and second module support structures at a center of each is less than a second gap formed at each step.

9. The detector assembly of claim 8, wherein the first and second module support structures each include a first surface and a second surface at a first step height, and the first and second module support structures each include a third surface at a second step height that is different from the first step height.

10. The detector assembly of claim 9, wherein the second height is closer to the focal spot than the first height.

11. The detector assembly of claim 9, wherein:
the third surface passes through the center of each of the first and second module support structures;
the first surface is at a first end of each of the first and second module support structures; and
the second surface is at a second end, opposite the first end, of each of the first and second module support structures.

12. The detector assembly of claim 9, wherein a first step of the two steps is between the third surface and the first surface, and a second step of the two steps is between the third surface and the second surface.

13. The detector assembly of claim 8, each detector module further comprising:
a substrate;
a photodiode positioned on the substrate;
a scintillating array positioned on the photodiode; and
the collimating elements aligned with a grid of pixels within the scintillating array.

14. The detector assembly of claim 8, wherein the plurality of detector modules are positioned along an arc along the channel direction such that the plurality of detector modules are each equidistant to the focal spot.

15. A method of manufacturing a CT detector, comprising:
positioning an array of module support structures along a channel direction of a CT system, each module support structure having module support surfaces extending along a Z-axis of the CT system, the array including a first module support structure and a second module support structure that are side-by-side; and
positioning a plurality of detector modules on each module support structure and having collimating elements that are generally aligned toward a focal spot of the CT system when positioned on a respective module support surface;
wherein each of the first and second module support structures includes two steps symmetrically disposed along the Z-axis, such that a first gap between the detector modules of the first and second module support structures at a center of each is less than a second gap formed at each step.

16. The method of claim 15, wherein the first and second module support structures each include a first surface and a second surface at a first step height, and the first and second module support structures each include a third surface at a second step height that is different from the first step height.

17. The method of claim 16, wherein the second height is closer to the focal spot than the first height.

18. The method of claim 16, wherein:
the third surface passes through the center of each of the first and second module support structures;
the first surface is at a first end of each of the first and second module support structures; and
the second surface is at a second end, opposite the first end, of each of the first and second module support structures.

19. The method of claim 16, wherein a first step of the two steps is between the third surface and the first surface, and a second step of the two steps is between the third surface and the second surface.

20. The method of claim 15, wherein the plurality of detector modules are positioned along an arc along the channel direction such that the plurality of detector modules are each equidistant to the focal spot.

* * * * *